(12) United States Patent
Deshpande et al.

(10) Patent No.: US 7,339,055 B2
(45) Date of Patent: *Mar. 4, 2008

(54) PROCESS FOR THE PREPARATION OF CEPHALOSPORIN ANTIBIOTIC

(75) Inventors: Pandurang Balwant Deshpande, Chennai (IN); Udayampalayam Palanisamy Senthilkumar, Erode District (IN); Velladurai Hero, Nagapattinam District (IN)

(73) Assignee: Orchid Chemicals & Pharmaceuticals Ltd., Chennai (IN)

( * ) Notice: Subject to any disclaimer, the term of this patent is extended or adjusted under 35 U.S.C. 154(b) by 424 days.

This patent is subject to a terminal disclaimer.

(21) Appl. No.: 10/922,991

(22) Filed: Aug. 23, 2004

(65) Prior Publication Data

US 2005/0080070 A1   Apr. 14, 2005

(30) Foreign Application Priority Data

Aug. 22, 2003   (IN)   .......................... 673/CHE/2003

(51) Int. Cl.
  C07D 501/56   (2006.01)
  C07D 501/36   (2006.01)
  C07D 501/34   (2006.01)
  C07D 501/22   (2006.01)

(52) U.S. Cl. .................... 540/215; 540/222; 540/225; 540/227; 540/228

(58) Field of Classification Search .................... None
See application file for complete search history.

(56) References Cited

U.S. PATENT DOCUMENTS

| | | | |
|---|---|---|---|
| 4,298,529 A | | 11/1981 | Ueda et al. |
| 4,409,215 A | * | 10/1983 | Takaya et al. ............... 514/207 |
| 4,464,367 A | | 8/1984 | Labeeuw et al. |
| 4,559,334 A | * | 12/1985 | Takaya et al. ............... 514/202 |
| 4,937,330 A | | 6/1990 | Sacks et al. |
| 4,960,766 A | * | 10/1990 | Takaya et al. ............... 514/202 |
| 5,089,490 A | * | 2/1992 | Durckheimer et al. ...... 514/206 |
| 5,109,131 A | | 4/1992 | Naito et al. |
| 6,458,949 B1 | | 10/2002 | Handa et al. |
| 6,552,186 B2 | | 4/2003 | Gerlach et al. |
| 6,777,549 B2 | | 8/2004 | Gerlach et al. |
| 6,800,756 B2 | * | 10/2004 | Deshpande et al. ......... 540/226 |
| 6,919,449 B2 | * | 7/2005 | Deshpande et al. ......... 540/222 |
| 7,098,329 B2 | * | 8/2006 | Deshpande et al. ......... 540/227 |
| 2005/0020561 A1 | | 1/2005 | Kumar et al. |
| 2005/0027118 A1 | * | 2/2005 | Deshpande et al. ......... 540/223 |
| 2005/0043531 A1 | * | 2/2005 | Handa et al. ............... 540/224 |
| 2005/0059820 A1 | | 3/2005 | Datta et al. |
| 2005/0119244 A1 | * | 6/2005 | Monguzzi et al. .......... 514/202 |
| 2005/0119478 A1 | * | 6/2005 | Monguzzi et al. .......... 540/227 |

(Continued)

FOREIGN PATENT DOCUMENTS

CA   1146165   5/1983

(Continued)

OTHER PUBLICATIONS

U.S. Appl. No. 11/240,382, filed Oct. 3, 2005.

Primary Examiner—Mark L. Berch
(74) Attorney, Agent, or Firm—Oliff & Berridge, PLC

(57) ABSTRACT

A process for the preparation of cephalosporin antibiotic of the formula (I)

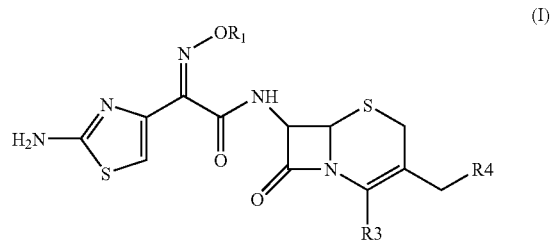

(I)

which comprises:
(i) activating the compound of formula (III) as acid halide in an organic solvent

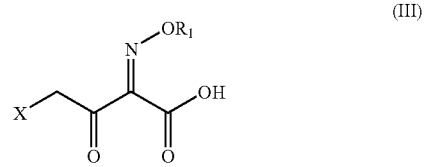

(III)

(ii) treating the reaction mass obtained from step (i) with water
(iii) separating the organic layer containing the reactive derivative of formula (III) and condensing it with 7-amino cephalosporin derivative by maintaining the pH in the range 5.0-10.0 using an inorganic base of the formula (XV), and
iv) cyclizing the compound of formula (XVI)

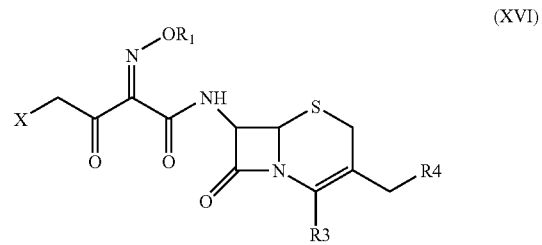

(XVI)

with thiourea in the presence of solvent and salt of organic or inorganic acid at a temperature in the range of −50 to +50° C. to produce compound of formula (I).

8 Claims, No Drawings

U.S. PATENT DOCUMENTS

2006/0058281 A1* 3/2006 Senthilkumar et al. ..... 514/203
2006/0094872 A1* 5/2006 Senthilkumar et al. ..... 540/217
2006/0100424 A1* 5/2006 Manca et al. ............... 540/200

FOREIGN PATENT DOCUMENTS

| | | |
|---|---|---|
| EP | 0 030 294 A2 | 6/1981 |
| EP | 160563 A2 * | 11/1985 |
| EP | 0 842 937 A2 | 5/1998 |
| GB | 2 012 276 A1 | 7/1979 |
| WO | WO 00/63214 | 10/2000 |
| WO | WO 02/083634 A2 | 10/2002 |
| WO | WO 2004/058695 A1 | 7/2004 |
| WO | WO 2004/092183 A2 | 10/2004 |

* cited by examiner

PROCESS FOR THE PREPARATION OF CEPHALOSPORIN ANTIBIOTIC

FIELD OF THE INVENTION

The present invention relates to a process for the preparation of cephalosporin antibiotic of the formula (I)

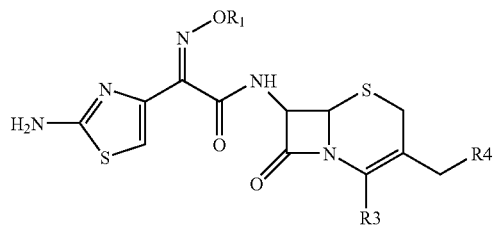

wherein $R_1$ represents hydrogen, trityl, $CH_3$, $CR_aR_bCOOR_c$ where $R_a$ and $R_b$ independently represent hydrogen or methyl and $R_c$ represents hydrogen or ($C_1$-$C_6$)alkyl; $R_3$ is carboxylate ion or $COOR_d$, where $R_d$ represents hydrogen, ester or a counter ion which forms a salt; $R_4$ represents H, $OCH_3$, $OCOCH_3$, $=CH_2$, $OCONH_2$,

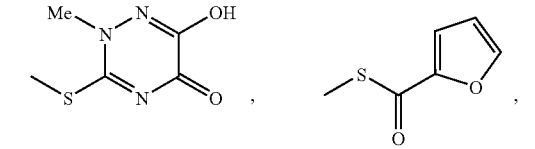

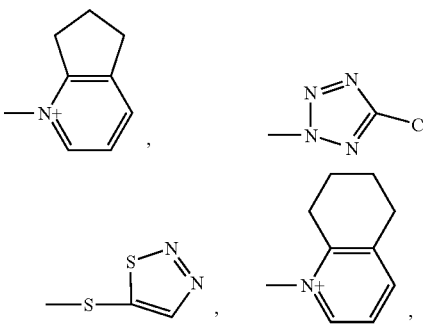

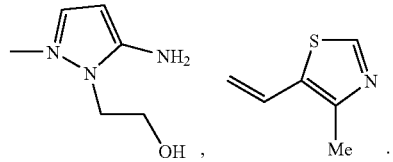

BACKGROUND OF THE INVENTION

EP 0030294 discloses a process for the preparation of compound of cephalosporin antibiotic as given in scheme 1:

Scheme 1

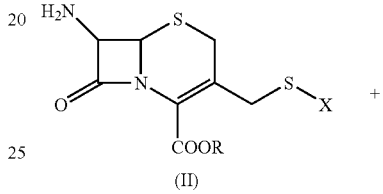

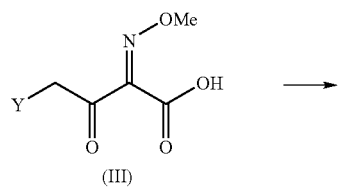

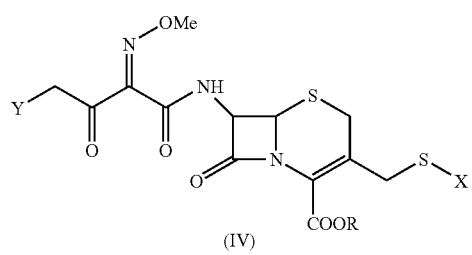

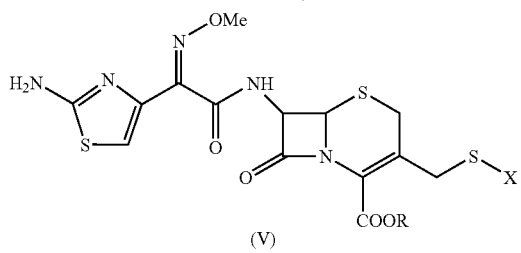

wherein R represents hydrogen atom or a readily hydrolysable ester group and X represents one of the groups

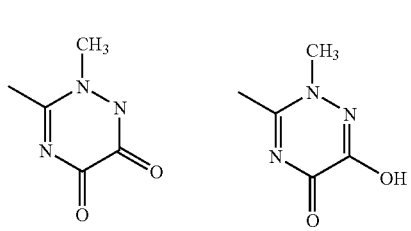

EP patent 0 842 937 discloses a process for the preparation of compound of cephalosporin antibiotic as given in scheme 2:

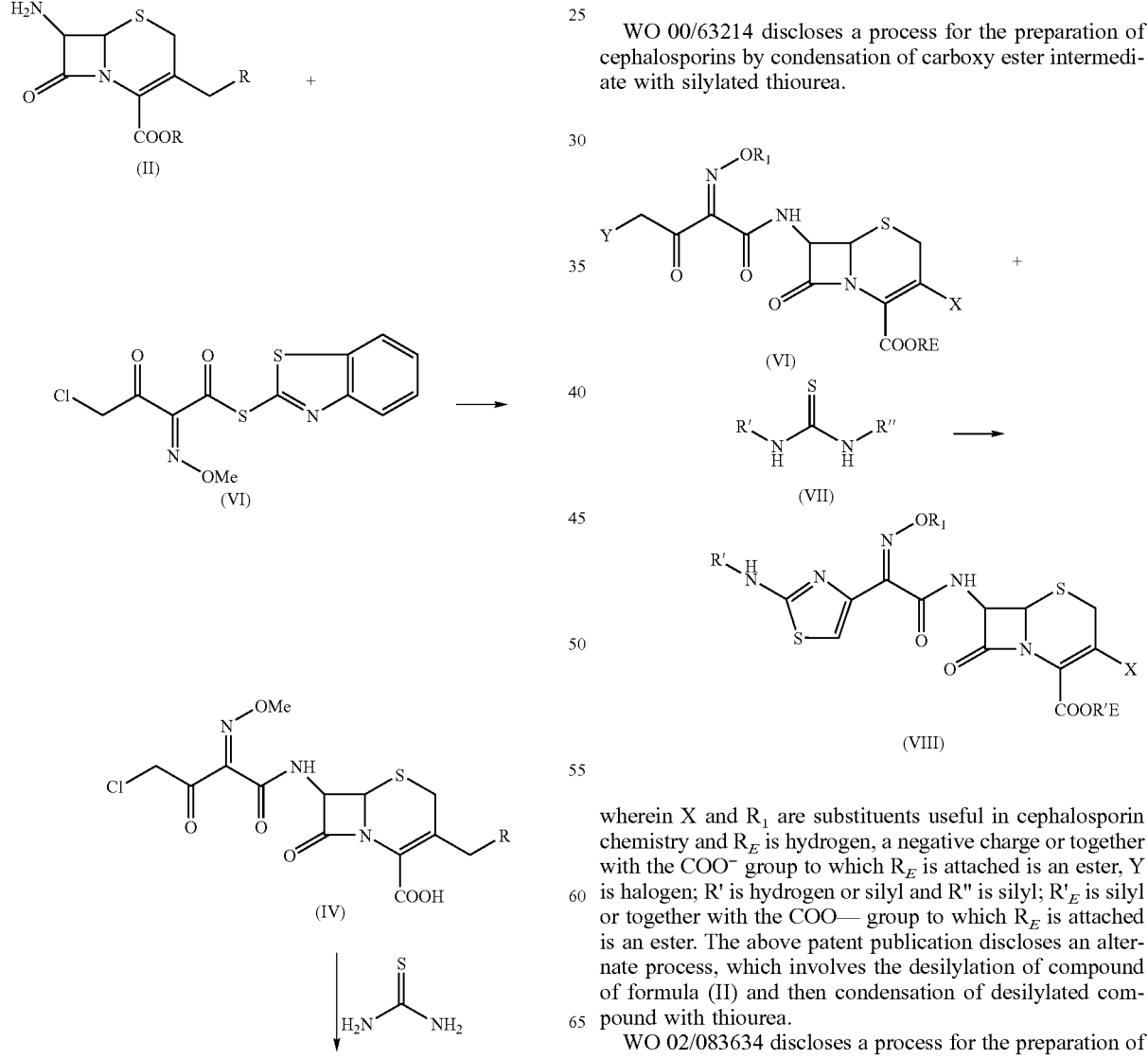

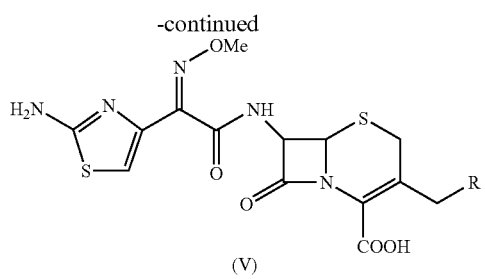

wherein R is

WO 00/63214 discloses a process for the preparation of cephalosporins by condensation of carboxy ester intermediate with silylated thiourea.

wherein X and $R_1$ are substituents useful in cephalosporin chemistry and $R_E$ is hydrogen, a negative charge or together with the COO⁻ group to which $R_E$ is attached is an ester, Y is halogen; R' is hydrogen or silyl and R" is silyl; $R'_E$ is silyl or together with the COO— group to which $R_E$ is attached is an ester. The above patent publication discloses an alternate process, which involves the desilylation of compound of formula (II) and then condensation of desilylated compound with thiourea.

WO 02/083634 discloses a process for the preparation of cefpodoxime of formula (I), as shown in scheme 3 below:

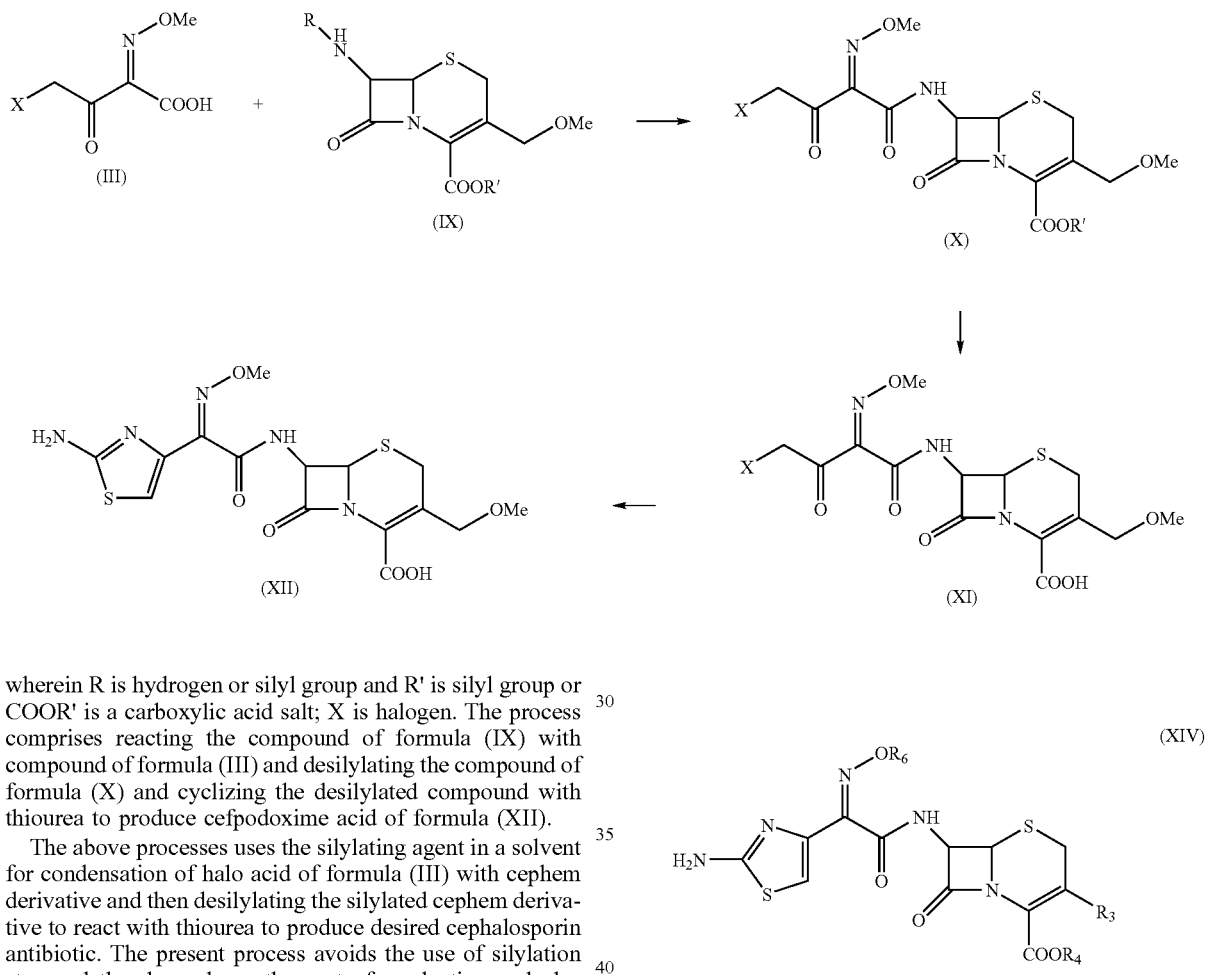

Scheme 3 wherein R is hydrogen or silyl group and R' is silyl group or COOR' is a carboxylic acid salt; X is halogen. The process comprises reacting the compound of formula (IX) with compound of formula (III) and desilylating the compound of formula (X) and cyclizing the desilylated compound with thiourea to produce cefpodoxime acid of formula (XII).

The above processes uses the silylating agent in a solvent for condensation of halo acid of formula (III) with cephem derivative and then desilylating the silylated cephem derivative to react with thiourea to produce desired cephalosporin antibiotic. The present process avoids the use of silyation step and thereby reduces the cost of production and also makes the process simple and easy to implement in commercial scale.

GB 2012276 describes 7-(4-halogeno-3-oxo-2-alkoxyiminobutyrylamino) cephalosporin derivative of the formula (XIII)

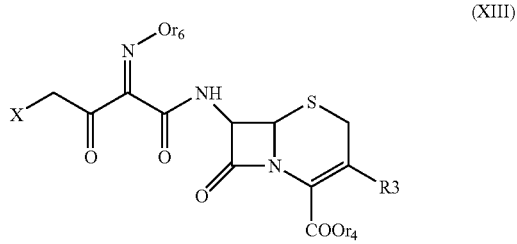

(XIII)

wherein X represents a halogen atom, $R^3$ represents —$CH_2R^5$ ($R^5$ is hydrogen atom or the residue of a nucleophilic compound), a halogen atom, an alkoxyl group, thiol group, amino group etc., —$COOR^4$ represents a carboxylic group which may be esterified, and $R^6$ represents an alkyl group and also a process for preparing a 7-[2-(2-aminothiazol-4-yl)-2-(syn)-alkoxyiminoacetamido]cephalosporin derivatives of the formula (XIV)

(XIV)

wherein the symbols have the same meanings as defined above, which comprises reacting the above compound (I) with thiourea. This patent also describes a process for the preparation of compounds of formula (XIII), which comprises reacting the compound of formula (III) or its reactive derivative with compound of formula (IX) using organic amine.

OBJECTIVES OF THE INVENTION

The primary objective of the invention is to provide an improved process for the preparation of cephalosporin antibiotic of the formula (I), which would be easy to implement in commercial scales.

Another objective of the present invention is to provide a process for removing byproduct at the stage of acid halide preparation itself by treating it with water at low temperatures, thereby yield cephalosporin antibiotic of the formula (I) in high purity and yield.

Another objective of the present invention is to provide a simple process for producing cephalosporin antibiotic of the formula (I), which avoids the use of silyation and desilylation, thereby reducing the cost of production and increasing the productivity.

SUMMARY OF THE INVENTION

Accordingly, the present invention provides a process for the preparation of cephalosporin antibiotic of the formula (I)

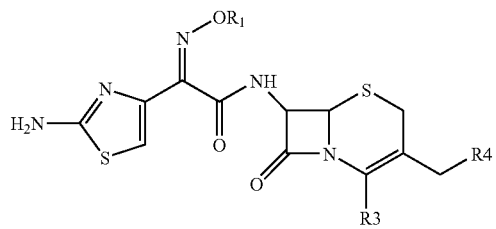

(I)

wherein $R_1$ represents hydrogen, trityl, $CH_3$, $CR_aR_bCOOR_c$ where $R_a$ and $R_b$ independently represent hydrogen or methyl and $R_c$ represents hydrogen or $(C_1-C_6)$alkyl; $R_3$ is carboxylate ion or $COOR_d$, where $R_d$ represents hydrogen, ester or a counter ion which forms a salt; $R_4$ represents H, $OCH_3$, $OCOCH_3$, $=CH_2$, $OCONH_2$,

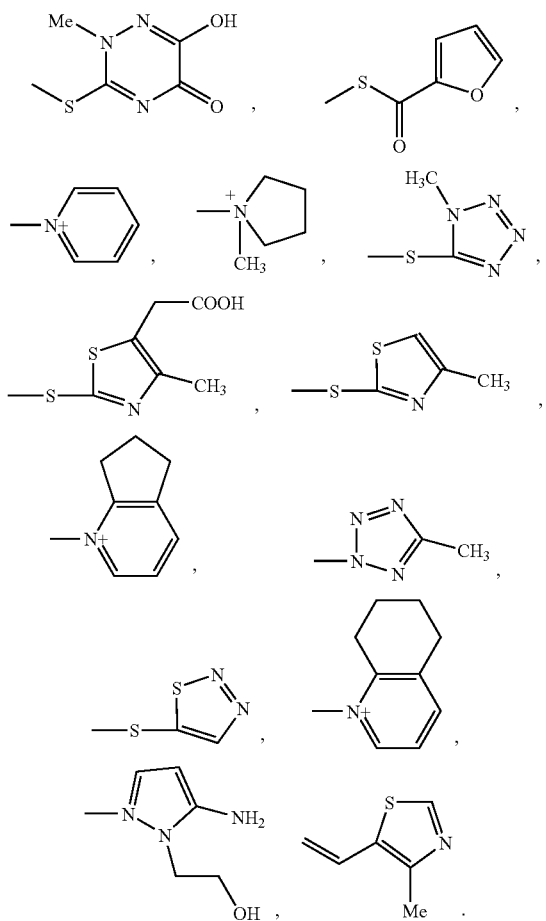

which comprises:
(i) activating the compound of formula (III) as acid halide in an organic solvent

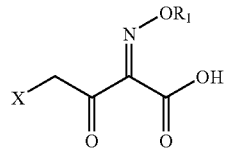

(III)

where X represents halogen atom such as chlorine or bromine, and $R_1$ is as defined above,
(ii) treating the reaction mass obtained from step (i) with water at a temperature in the range of $-40°$ C. to $+10°$ C.,
(iii) separating the organic layer containing the reactive derivative of formula (III) and condensing it with 7-amino cephalosporin derivative of the formula (XV)

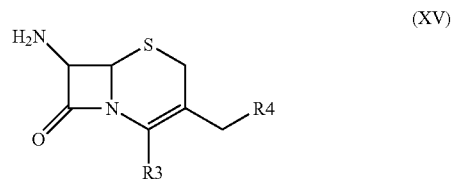

(XV)

in the presence of a solvent at a temperature in the range of $-50°$ C. to $+50°$ C. by maintaining the pH in the range 5.0-10.0 using an inorganic base to produce a compound of formula (XVI)

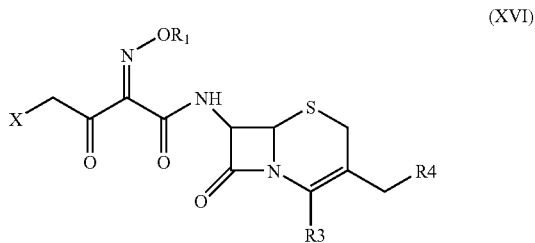

(XVI)

where all symbols are as defined above, and
iv) cyclizing the compound of formula (XVI) with thiourea in the presence of solvent and salt of organic or inorganic acid at a temperature in the range of $-50$ to $+50°$ C. to produce compound of formula (I).

DETAILED DESCRIPTION OF THE INVENTION

In an embodiment of the present invention, the solvent used in step (i) is selected from halogenated hydrocarbon like dichloromethane; esters like ethyl acetate or mixtures thereof In another embodiment of the present invention, the condensation of compound of formula (III) with (XV) in step (iii) is performed by using the reactive derivative of formula (III) in the presence of a solvent selected from dichloromethane, ethyl acetate, methanol, ethanol, isopropanol, isobutyl alcohol, n-propanol, n-butanol, tert-butanol, tetrahydrofuran, aromatic hydrocarbons, acetone, ethyl methyl ketone, diethyl ketone, pentan-3-one, cyclohexanone, methyl isobutyl ketone, dioxane, acetonitrile, DMAc, N,N-dimethylformamide, dialkylethers, ethylene glycol, ethylene glycol monomethyl ether, diglyme, monoglyme, diethylene glycol, triethylene glycol, polyethylene glycol, water and the like or mixtures thereof.

In still another embodiment of the present invention, the inorganic base used for maintaining the pH is selected from ammonia; sodium carbonate, sodium bicarbonate, ammonium carbonate, potassium carbonate, sodium hydroxide, potassium hydroxide and the like.

In yet another embodiment of the present invention, the compound of formula (III) is activated as acid halides using halogenating agent like $PCl_5$, $PCl_3$, $POCl_3$ and the like; mixed anhydrides, active esters, active amides. The acid halides are acid chlorides or acid bromides. The mixed anhydrides are anhydrides of the compounds of formula (III) with pivaloyl chloride, ethyl chloroformate, benzyl chloroformate.

In yet another embodiment of the present invention the cyclization of compound of (XVI) is carried out using solvents selected from water, tetrahydrofuran, acetone, ethyl methyl ketone, methyl isobutyl ketone, methyl isopropyl ketone, cyclohexanone, diethyl ketone, pentan-3-one, cyclohexanone, acetonitrile, N,N-dimethylformamide, N,N-dimethylacetamide, dioxane, $(C_1-C_5)$alcohol, ethylene glycol, diglyme, monoglyme, ethylene glycol monomethyl ether, diethylene glycol, triethylene glycol, polyethylene glycol and the like or mixtures thereof.

In another embodiment of the present invention, salts of organic or inorganic acid is selected from sodium acetate, sodium carbonate, sodium bicarbonate, potassium acetate, ammonium acetate, ammonium carbonate, barium carbonate, calcium carbonate, potassium carbonate, barium carbonate, lithium carbonate, potassium bicarbonate, sodium methoxide, or sodium ethoxide and the like.

In yet another embodiment of the present invention, there is provided a process for the purification of compound of formula (I) by crystallizing or precipitating the compound in a solvent mixture selected from water, methanol, acetone, 2-butanone, pentan-2-one, pentan-3-one, MIBK, ethyl acetate, ethanol, propanol, isobutanol and the like and isolating the pure compound by conventional methods.

In an embodiment of the present invention the acid chloride is treated with water at low temperature, which helps in removing all the acidic impurities like $POCl_3$, and other byproduct, which are responsible for the formation of anti isomer in final product.

In another embodiment of the present invention is the compound of formula (I) obtained in syn isomer.

In yet another embodiment of the present invention the reaction is carried out in a single pot.

In one more embodiment of the present invention the compound of formula (I) can be converted into its pharmaceutically acceptable salt or hydrates or esters or its prodrugs by conventional methods.

The present invention is provided by the examples below, which are provided by way of illustration only and should not be considered to limit the scope of the invention.

EXAMPLE 1

Cefepime Hydrochloride

Preparation of Cefepime Sulfate

To dichloromethane (300 mL), 4-chloro-2-methoxy-imino-3-oxobutyric acid (50 g) was added under stirring to get a clear solution at 23-28° C. and cooled to −5 to 0° C. under nitrogen. To the cold solution, phosphorous pentachloride (64 g) was added under nitrogen and stirred for 30-40 min. The reaction mixture was cooled to −25 to −20° C. and cold water (500 mL) added to it. The organic layer was separated and charged into 7-amino-3-((N-methylpyrrolidino)methyl)-3-cephem-$4$-carboxylic acid (100 g) in aqueous acetone (700 mL) at −5 to 0° C. over a period of 30-40 min while maintaining the pH in the range 6.0-7.0 using dil. ammonia solution (15%). Thiourea (28 g), and sodium acetate trihydrate (56 g) were added to the reaction mixture at −5 to 0° C. The temperature of the reaction mixture was allowed to rise to 18-20° C. Sodium acetate (14 g) was added and stirred for 2 h and the aqueous layer separated. To the aqueous layer, water & dil. sulphuric acid were added to adjust the pH to 1.1-1.2 at 15-20° C., followed by excess acetone (2100 mL) at 35-40° C. The resulting slurry was cooled to 0-2° C., filtered, and washed with water and acetone. The material was dried under vacuum & taken for purification.

Purification of Cefepime Sulfate

To a stirred mixture of water (630 mL) and cefepime sulfate (140 g), triethylamine was added (37 mL) up to a pH of 3.5-3.6. The clear solution was charcoalized and washed with water. The filtrate was warmed to 38-42° C., & the pH adjusted to 1.1-1.2 with dil. sulfuric acid. The resulting slurry was cooled to 27-30° C. over 60 min, filtered and washed with water and acetone. Drying under vacuum afforded pure cefepime sulfate.

Preparation of Cefepime Hydrochloride

To a stirred mixture of water (273 mL) and ethyl acetate (70 mL), cefepime sulfate (70 g) was added at 18-20° C. A solution of amberlite LA-2 resin (155 mL) in ethyl acetate (635 mL) & acetic acid (15 mL) was added over a period of 45-60 min while maintaining the pH 4.2-4.4. The aqueous layer was separated and the organic layer extracted with water. The aqueous layers were combined and charcoalized. The filtrate was warmed to 25-30° C. and the pH adjusted to 0.7-0.8 with hydrochloric acid. Acetone (2100 mL) was added over 75 min at 35-38° C. under stirring. The product obtained was cooled to 0-2° C., filtered, and washed with aqueous acetone and acetone. Drying under vacuum afforded pure cefepime hydrochloride.

EXAMPLE 2

Preparation of Ceftriaxone Acid

4-Chloro-2-methoxyimino-3-oxobutyric acid (17.4 g) was added to dichloromethane (100 mL) at 25-30° C. The clear solution obtained was cooled to −5 to 0° C. under nitrogen. To the cold solution, phosphorous pentachloride (22.2 g) at −5 to 0° C. under nitrogen. After stirring for a period of 1 h at this temperature, the reaction mixture was cooled to −35 to −30° C. under nitrogen. To the reaction mixture, cold water (100 mL) was added at −5 to 0° C. and the organic layer separated. The organic layer was added to 7-ACT ((6R,7R)-7-amino-3-[[(2,5-dihydro-6-hydroxy-2-methyl-5-oxo-1,2,4-triazin-3-yl)thio]methyl]-8-oxo-5-thia-1-azabicyclo[4.2.0]oct-2-ene-2-carboxylic acid) (20 g) in aqueous acetone (200 mL) at −10 to 0° C. in 30-40 min while maintaining the pH 9.8-7.0 using dil. ammonia. The pH of the reaction mixture was maintained until completion of the reaction. The aqueous layer was separated at −5 to 0° C. To the aqueous layer, thiourea (7.26 g) and sodium acetate trihydrate (21.8 g) were added and the temperature raised to 2-5° C. The reaction mixture was stirred for 18-24 h. The reaction mixture was diluted with water and charcoalized. To the filtrate, dil sulfuric acid was added to set the pH~2.5 over a period of 2-3 h. The product, ceftriaxone acid, obtained was separated by filtration and washed with water. The wet material of ceftriaxone acid was taken for conversion to ceftriaxone sodium as shown below.

Preparation of Ceftriaxone Sodium & Purification

The ceftriaxone acid was dissolved in aqueous acetone using triethylamine. To the clear solution obtained, sodium acetate trihydrate (13 g) was added and. charcoalized. To the filtrate, acetone (720 mL) was added over 1-2 h and filtered to get ceftriaxone sodium. The wet material of ceftriaxone sodium thus obtained was dissolved in water (120 mL) followed by addition of acetone (222 mL). The solution was cooled to −5 to −15° C. and the impurity separated as a sticky mass. The clear solution was separated and the temp raised to 18-22 C. Acetone (624 mL) was added under stirring over 1 h, filtered and washed with acetone. Drying under vacuum afforded pure ceftriaxone sodium (19.2 g).

EXAMPLE 3

Preparation of Ceftriaxone Acid

4-Chloro-2-methoxyimino-3-oxobutyric acid (17.4 g) was added to dichloromethane (100 mL) at 25-30° C. The clear solution obtained was cooled to −5 to 0° C. under nitrogen. To the cold solution, phosphorous pentachloride (22.2 g) at −5 to 0° C. under nitrogen. After stirring for a period of 1 h at this temperature, the reaction mixture was cooled to −35 to −30° C. under nitrogen. To the reaction mixture, cold water (100 mL) was added at −5 to 0° C. and the organic layer separated. The organic layer was added to 7-ACT (20 g) in aqueous methanol (180 mL) at −10 to 0° C. in 30-40 min while maintaining the pH 9.8-7.0 using dil. ammonia. The pH of the reaction mixture was maintained until completion of the reaction. The aqueous layer was separated at −5 to 0° C. To the aqueous layer, thiourea (7.26 g) and sodium acetate trihydrate (21.8 g) were added and the temperature raised to 2-5° C. The reaction mixture was stirred for 18-24 h. The reaction mixture was diluted with water and charcoalized. To the filtrate, dil sulfuric acid was added to set the pH~2.5 over a period of 2-3 h. The product, ceftriaxone acid, obtained was separated by filtration and washed with water. The wet material of ceftriaxone acid was taken for conversion to ceftriaxone sodium as shown below.

Preparation of Ceftriaxone Sodium & Purification

The ceftriaxone acid was dissolved in aqueous acetone using triethylamine. To the clear solution obtained, sodium acetate (13 g) was added and charcoalized. To the filtrate, acetone (720 mL) was added over 1-2 h and filtered to get ceftriaxone sodium. The wet material of ceftriaxone sodium thus obtained was dissolved in water (120 mL) followed by addition of acetone (222 mL). The solution was cooled to −5 to −15° C. and the impurity separated as a sticky mass. The clear solution was separated and the temp raised to 18-22 C. Acetone (624 mL) was added under stirring over 1 h, filtered and washed with acetone. Drying under vacuum afforded pure ceftriaxone sodium (19.2 g).

EXAMPLE 4

Preparation of Ceftriaxone Acid

{(6R,7R)-7-[2-(2-Amino-4-thiazolyl)-2[(Z)-methoxyimino]acetamido]-3-[[(2,5-dihydro-6-hydroxy-2methyl-5-oxo-as-triazin-3-yl)thio]methyl]-8-oxo-5-thia-1-azabicylo[4.2.0]oct-2-ene-2-carboxylic acid}

4-Chloro-2-methoxyimino-3-oxobutyric acid (17.4 g) was added to dichloromethane (100 mL) at 25-30° C. The clear solution obtained was cooled to −5 to 0° C. under nitrogen. To the cold solution, phosphorous pentachloride (22.2 g) at −5 to 0° C. under nitrogen. After stirring for a period of 1 h at this temperature, the reaction mixture was cooled to −35 to −30° C. under nitrogen. To the reaction mixture, cold water (100 mL) was added at −5 to 0° C. and the organic layer separated. The organic layer was added to 7-ACT (20 g) in aqueous polyethyleneglycol (200 mL) at −10 to 0° C. in 30-40 min while maintaining the pH 9.8-7.0 using dil. ammonia. The pH of the reaction mixture was maintained until completion of the reaction. The aqueous layer was separated at −5 to 0° C. To the aqueous layer, thiourea (7.26 g) and sodium acetate trihydrate (21.8 g) were added and the temperature raised to 2-5° C. The reaction mixture was stirred for 18-24 h. The reaction mixture was diluted with water and charcoalized. To the filtrate, dil sulfuric acid was added to set the pH~2.5 over a period of 2-3 h. The product, ceftriaxone acid, obtained was separated by filtration and washed with water. The wet material of ceftriaxone acid was taken for conversion to ceftriaxone sodium as shown below.

Preparation of Ceftriaxone Sodium & Purification

The ceftriaxone acid was dissolved in aqueous acetone using triethylamine. To the clear solution obtained, sodium acetate (13 g) was added and charcoalized. To the filtrate, acetone (720 mL) was added over 1-2 h and filtered to get ceftriaxone sodium. The wet material of ceftriaxone sodium thus obtained was dissolved in water (120 mL) followed by addition of acetone (222 mL). The solution was cooled to −5 to −15° C. and the impurity separated as a sticky mass. The clear solution was separated and the temp raised to 18-22 C. Acetone (624 mL) was added under stirring over 1 h, filtered and washed with acetone. Drying under vacuum afforded pure ceftriaxone sodium.

EXAMPLE 5

Preparation of Cefotaxime

{ (6R,7R)-3-(Acetoxymethyl)-7-[2-(2-aminothiazol-4-yl)-2-(methoxyimino)acetamido]8-oxo-5-thia-1-azabicyclo[4.2.0]oct-2-ene-2-carboxylic acid}

4-Chloro-2-methoxyimino-3-oxobutyric acid (20 g) was added to dichloromethane (120 mL) at 25-30° C. The clear solution obtained was cooled to −5 to 0° C. under nitrogen. To the cold solution, phosphorous pentachloride (25 g) at −5 to 0° C. under nitrogen. After stirring for a period of 1 h at this temperature, the reaction mixture was cooled to −30 to −25° C. under nitrogen. To the reaction mixture, cold water (250 mL) was added at −5 to 0° C. and the organic layer separated. The organic layer was added to 7-aminocephalosporanic acid (25 g) in aqueous acetone (175 mL) at −5 to 0° C. in 30-40 min while maintaining the pH at 6.5-7.0 using dil. ammonia (15%). The pH of the reaction mixture was maintained until completion of the reaction. To the reaction mixture, thiourea (11 g) and sodium acetate trihydrate (22 g) were added and the temperature raised to 18-20° C. The reaction mixture was stirred for 1 h. To the reaction mixture, dil HCl was added to set the pH~3.0 over a period of 30-40 min to crystallize the product. Cold water was added and the product was obtained by filtration and washing with water and acetone.

EXAMPLE 6

Purification of Cefepime Hydrochloride

{(6R,7R)-7-[2-(2-Aminothiazol-4-yl)-2(Z)-(methoxyimino)acetamido]-3-(1-methylpyrrolidiniomethyl)-3-cephem-4-carboxylate}

Methanol (500 ml) was charged into a RB flask and cooled to 20-25° C. To this cefepime hydrochloride was added and stirred to get clear solution. The solution was stirred with charcoal for 25-30 minutes at 20-25° C. The charcoal was filtered off. To the clear filtrate acetone (330 ml) was added in 20-25 minute. The solution was stirred for 1 hr and acetone (700 ml) was added to this solution to precipitate the solid. The solid was filtered and washed with acetone (2×150 ml) and dried under vacuum to afford pure cefepime hydrochloride

EXAMPLE 7

Purification of Ceftriaxone Sodium

Ceftriaxone sodium (20 gm) was dissolved in aqueous acetone (60 ml) and cooled to 20-25° C. To the clear solution acetone (13 ml) and EDTA (0.02 gm) were added. The resultant solution was charcoalized and filtered. The charcoal was filtered off. To the clear filtrate acetone (313 ml) was added in 110-120 minute. The precipitated solid was stirred for 30 min at 2-5° C. and filtered. The solid was washed with acetone (80 ml), dried the solid at 35 to 40° C. under vacuum to afford pure ceftriaxone sodium.

EXAMPLE 8

Preparation of Ceftriaxone Acid

4-Chloro-2-methoxyimino-3-oxobutyric acid (17.4 g) was added to dichloromethane (100 mL) at 25-30° C. The clear solution obtained was cooled to −5 to 0° C. under nitrogen. To the cold solution, phosphorous pentachloride (22.2 g) at −5 to 0° C. under nitrogen. After stirring for a period of 1 h at this temperature, the reaction mixture was cooled to −35 to −30° C. under nitrogen. To the reaction mixture, cold water (100 mL) was added at −5 to 0° C. and the organic layer separated. The organic layer was added to 7-ACT ((6R,7R)-7-amino-3-[[(2,5-dihydro-6-hydroxy-2-methyl-5-oxo-1,2,4-triazin-3-yl)thio[methyl]-8-oxo-5-thia-1-azabicyclo[4.2.0]oct-2-ene-2-carboxylic acid) (20 g) in aqueous acetone (200 mL) at −10 to 0° C. in 30-40 min while maintaining the pH 9.8-7.0 using dil. ammonia. The pH of the reaction mixture was maintained until completion of the reaction. To the reaction mass, thiourea (7.26 g) and sodium acetate trihydrate (21.8 g) were added and the temperature raised to 2-5° C. The reaction mixture was stirred for 18-24 h. The aqueous layer was separated and diluted with water and charcoalized. To the filtrate, dil sulfuric acid was added to set the pH~2.5 over a period of 2-3 h. The product, ceftriaxone acid, obtained was separated by filtration and washed with water. The wet material of ceftriaxone acid was taken for conversion to ceftriaxone sodium.

EXAMPLE 9

Cefepime Hydrochloride

Preparation of Cefelpime Sulfate

To dichloromethane (300 mL), 4-chloro-2-methoxy-imino-3-oxobutyric acid (50 g) was added under stirring to get a clear solution at 23-28° C. and cooled to −5 to 0° C. under nitrogen. To the cold solution, phosphorous pentachloride (64 g) was added under nitrogen and stirred for 30-40 min. The reaction mixture was cooled to −25 to −20° C. and cold water (500 mL) added to it. The organic layer was separated and charged into 7-amino-3-((N-methylpyrrolidino)methyl)-3-cephem-4-carboxylic acid (100 g) in aqueous acetone (700 mL) at −5 to 0° C. over a period of 30-40 min while maintaining the pH in the range 6.0-7.0 using dil. ammonia solution (15%). Thiourea (28 g) was added to the reaction mixture at −5 to 0° C. The temperature of the reaction mixture was allowed to rise to 18-20° C. Sodium bicarbonate (20-25 g) was added over 2 h by maintaining pH at 5.0 to 5.5 and the aqueous layer separated. To the aqueous layer, water & dil. sulphuric acid were added to adjust the pH to 1.1-1.2 at 15-20° C., followed by excess acetone (2100 mL) at 35-40° C. The resulting slurry was cooled to 0-2° C., filtered, and washed with water and acetone. The material was dried under vacuum & taken for purification as shown in Step (ii).

Purification of Cefepime Sulfate

To a stirred mixture of water (630 mL) and cefepime sulfate (140 g), triethylarine was added (37 mL) up to a pH of 3.5-3.6. The clear solution was charcoalized and washed with water. The filtrate was warmed to 38-42° C., & the pH adjusted to 1.1-1.2 with dil. sulfuric acid. The resulting slurry was cooled to 27-30° C. over 60 min, filtered and washed with water and acetone. Drying under vacuum afforded pure cefepime sulfate.

Preparation of Cefepime Hydrochloride

To a stirred mixture of water (273 mL) and ethyl acetate (70 mL), cefepime sulfate (70 g) was added at 18-20° C. A solution of amberlite LA-2 resin (155 mL) in ethyl acetate (635 mL) & acetic acid (15 mL) was added over a period of 45-60 min while maintaining the pH 4.2-4.4. The aqueous layer was separated and the organic layer extracted with water. The aqueous layers were combined and charcoalized. The filtrate was warmed to 25-30° C. and the pH adjusted to 0.7-0.8 with hydrochloric acid. Acetone (2100 mL) was added over 75 min at 35-38° C. under stirring. The product obtained was cooled to 0-2° C., filtered, and washed with aqueous acetone and acetone. Drying under vacuum afforded pure cefepime hydrochloride.

What is claimed is:

1. A process for the preparation of cephalosporin antibiotic of the formula (I)

(I)

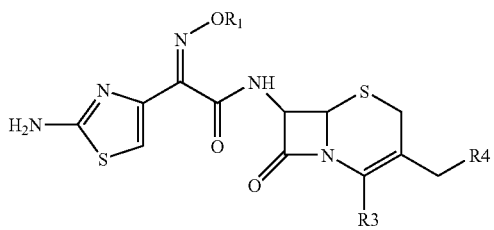

wherein $R_1$ represents hydrogen, trityl, $CH_3$, $CR_aR_bCOOR_c$ where $R_a$ and $R_b$ independently represent hydrogen or methyl and $R_c$ represents hydrogen or $(C_1-C_6)$alkyl; $R_3$ is carboxylate ion or $COOR_d$, where $R_d$ represents hydrogen, ester or a counter ion which forms a salt; $R_4$ represents H, $-OCH_3$, $-OCOCH_3$, $-OCONH_2$,

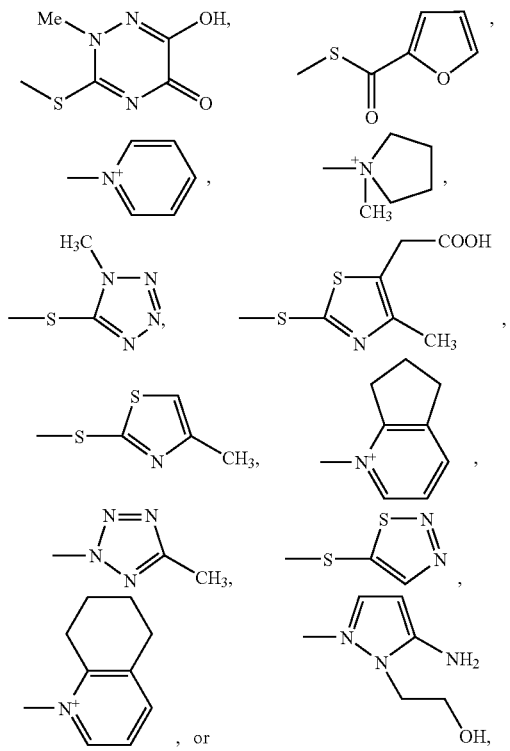

the process consisting of:
(i) activating the compound of formula (III) as acid halide in an organic solvent (III)

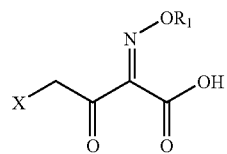

where X represents halogen atom such as chlorine or bromine, and $R_1$ is as defined above, (ii) treating a reaction mass obtained from step (i) at a temperature in the range of −40° C. to +10° C. with water, (iii) separating the organic layer containing the reactive derivative of a compound of formula (III) and condensing it with 7-amino cephalosporin derivative of the formula (XV)

(XV)

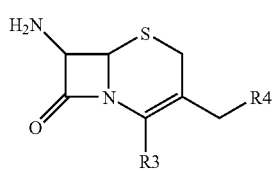

in the presence of a solvent at a temperature in the range of −50° C. to +50° C. by maintaining the pH in the range 5.0-10.0 using an inorganic base to produce a compound of formula (XVI)

(XVI)

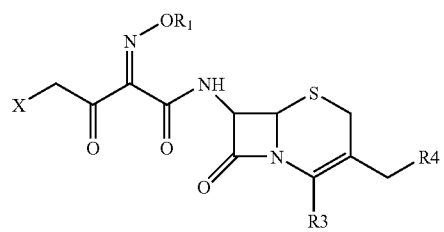

where all symbols are as defined above, wherein the organic layer from step (ii) containing the activated derivative of the compound of formula (III) is condensed with the 7-amino cephalosporin derivative of the formula (XV), and (iv) cyclizing the compound of formula (XVI) with thiourea in the presence of solvent and salt of organic or inorganic acid at a temperature in the range of −50 to +50° C. to produce compound of formula (I), wherein producing the compound of formula (I) occurs without isolating the compound of formula (XVI).

2. The process as claimed in claim 1, wherein the solvent in step (i) is selected from dichloromethane, ethyl acetate and mixtures thereof and the solvent for condensation in step (iii) is selected from dichloromethane, ethyl acetate, methanol, ethanol, isopropanol, isobutyl alcohol, n-propanol, n-butanol, tert-butanol, tetrahydrofuran, aromatic hydrocarbons, acetone, ethyl methyl ketone, diethyl ketone, pentan-3-one, cyclohexanone, methyl isobutyl ketone, dioxane, acetonitrile, N,N-dimethylacetamide, N,N-dimethylformamide, dialkylethers, ethylene glycol, ethylene glycol monomethyl ether, diglyme, monoglyme, diethylene glycol, triethylene glycol, polyethylene glycol, water and mixtures thereof.

3. The process as claimed in claim 1, wherein the inorganic base in step (iii) is selected from ammonia, sodium carbonate, sodium bicarbonate, ammonium carbonate, barium carbonate, lithium carbonate, potassium carbonate, sodium hydroxide and potassium hydroxide.

4. The process as claimed in claim 1, wherein the solvent for the cyclization is selected from water, tetrahydrofuran, acetone, ethyl methyl ketone, methyl isobutyl ketone, methyl isopropyl ketone, cyclohexanone, diethyl ketone, pentan-3-one, cyclohexanone, acetonitrile, N,N-dimethylformamide, N,N-dimethylacetamide, dioxane, $(C_1$-$C_5)$alcohol, ethylene glycol, diglyme, monoglyme, ethylene glycol monomethyl ether, diethylene glycol, triethylene glycol, polyethylene glycol and mixtures thereof.

5. The process as claimed in claim 1, wherein the salts of organic or inorganic acid are selected from sodium acetate, sodium carbonate, sodium bicarbonate, potassium acetate, ammonium acetate, ammonium carbonate, barium carbonate, calcium carbonate, potassium carbonate, barium carbonate, lithium carbonate, potassium bicarbonate, sodium methoxide, and sodium ethoxide.

6. The process as claimed in claim 1, wherein the purification of compound of formula (I) is carried out by crystallizing or precipitating the compound in a solvent.

7. The process as claimed in claim 6, wherein the solvent is selected from water, methanol, acetone, 2-butanone, pentan-2-one, pentan-3-one, methyl isobutyl ketone, ethyl acetate, ethanol, propanol, isobutanol and mixtures thereof.

8. The process as claimed in claim 1, further comprising converting the compound of formula (I) into pharmaceutical acceptable salts, hydrates, solvates, esters or its prodrug.

* * * * *